United States Patent [19]

Suzuki et al.

[11] Patent Number: 5,011,680

[45] Date of Patent: Apr. 30, 1991

[54] SOLID COSMETIC PREPARATION

[75] Inventors: Toshiyuki Suzuki, Ichikawa; Masahide Nohta, Sakura; Akira Shigeta, Tokyo; Yoshimitsu Ina, Funabashi; Manami Nozawa, Chiba, all of Japan

[73] Assignee: Kao Corporation, Tokyo, Japan

[21] Appl. No.: 208,792

[22] Filed: Jun. 15, 1988

Related U.S. Application Data

[63] Continuation of Ser. No. 837,615, Mar. 7, 1986, abandoned.

[30] Foreign Application Priority Data

| Mar. 13, 1985 [JP] | Japan | 60-50124 |
| Sep. 6, 1985 [JP] | Japan | 60-196973 |
| Sep. 6, 1985 [JP] | Japan | 60-196974 |

[51] Int. Cl.$^5$ ............... A61K 7/025; A61K 31/21; A61K 31/08
[52] U.S. Cl. ............... 424/64; 424/DIG. 5; 514/510; 514/723; 514/547; 514/844
[58] Field of Search ............... 424/64, 63, DIG. 5; 514/510, 723, 844, 547

[56] References Cited

U.S. PATENT DOCUMENTS

| 2,876,162 | 3/1959 | Lauffer | 424/64 |
| 3,937,811 | 2/1976 | Papantoniou et al. | 424/64 |
| 4,172,149 | 10/1979 | Pinto et al. | 424/312 |
| 4,309,448 | 1/1982 | Takaishi et al. | 514/785 |
| 4,348,415 | 9/1982 | Tsutsumi et al. | 424/70 X |
| 4,367,220 | 1/1983 | Boulogne et al. | 424/64 |
| 4,383,875 | 5/1983 | Russ et al. | 424/63 X |
| 4,390,524 | 6/1983 | Nasuno et al. | 424/69 X |
| 4,537,766 | 8/1985 | Russ et al. | 424/63 |
| 4,726,959 | 2/1988 | Momura et al. | 426/607 |

FOREIGN PATENT DOCUMENTS

| 3310094 | 6/1984 | Fed. Rep. of Germany . |
| 56-65900 | 6/1981 | Japan . |
| 57-88108 | 6/1982 | Japan | 514/723 |
| 57-120508 | 7/1982 | Japan | 424/64 |
| 57-130909 | 8/1982 | Japan . |
| 59-27808 | 2/1984 | Japan . |

Primary Examiner—John W. Rollins
Attorney, Agent, or Firm—Flynn, Thiel, Boutell & Tanis

[57] ABSTRACT

A fat and oil composition comprises (1) as the main triglyceride one or more mixed acid triglyceride having one or more saturated C20 to C24 fatty acid residue and one or more unsaturated C16 to C22 fatty acid residue in a molecule thereof and (2) in the entire fatty acid moiety 15 to 70 wt. % of one or more saturated C20 to C24 fatty acids and 20 to 60 wt. % of one or more unsaturated C16 to C22 fatty acids. It is useful as a base of a solid cosmetic preparation.

18 Claims, 1 Drawing Sheet

SOLID COSMETIC PREPARATION

This application is a continuation of U.S. Ser. No. 837,615, filed Mar. 7, 1986 now abandoned.

The present invention relates to a solid cosmetic preparation, specifically to a solid cosmetic preparation comprising a plastic fat mainly consisting of a mixed acid triglyceride having residues of a straight-chain saturated fatty acid having 20 or more carbon atoms and an unsaturated fatty acid having 16 to 22 carbon atoms, said plastic fat containing, as the constituent fatty acids, 30 to 70 wt. % of said saturated fatty acid having 20 or more carbon atoms and 20 to 60 wt. % of said unsaturated fatty acid having 16 to 22 carbon atoms.

STATEMENT OF PRIOR ARTS

Representative solid cosmetic preparations include bar-like ones such as lipsticks, lip cream, foundation sticks, and stick pomade; pencil-like ones such as eyebrow pencils and eyeliner pencils; pressed powders such as foundation, eye shadow, and rouge; and oily cake-like ones.

Among them, conventional oily cosmetic preparations are those containing a powder dispersed in a mixed system of a solid fat such as carnauba wax, candelilla wax, ceresin, microcrystalline wax, hardened animal or vegetable oil, or beeswax, with a liquid or semi-liquid oil such as castor oil, olive oil, jojoba oil, squalane, a synthetic ester oil, silicone oil, liquid paraffin, or vaseline. Therefore, a difficulty is encountered in providing a homogeneous mixture system, and unbalanced compatibility appears with the lapse of time in storage and changes in temperature and humidity in a storage environment. This disadvantageously entails deterioration of the appearance quality due to sweating and blooming, and reductions in breaking strength and feeling in use thereof due to a large change in hardness (yield value). In cosmetic preparations of a pressed powder type having a high powder proportion, oil components as mentioned above are employed from the viewpoints of the touch in their use, the bonding power and shape retention in blending and forming. In this case, collapse, breakage or cracking due to poor impact resistance during the use are caused when the bonding power between particles is insufficient. In contrast, when the bonding power between particles is too strong, the bonding of them to a puff or brush is poor, resulting in difficult application of them, and the oily shininess leads to a poor appearance. These phenomena are hard to obviate only by controlling the forming conditions such as the pressure in pressing. In addition, Japanese patent publication (unexamined) A No. 57-130909 teaches a cosmetic preparation containing a mixed acid triglyceride having behenic acid and a branched, saturated fatty acid of 8 or more carbon atoms, but still involves some problems.

SUMMARY OF THE INVENTION

As a result of intensive investigations with a view to obviating the above-mentioned defects under such circumstances, the inventors of the present invention have found that an excellent cosmetic preparation can be obtained by blending, in its formulation, a plastic fat mainly consisting of a mixed acid triglyceride having residues of a straight-chain saturated fatty acid having 20 or more carbon atoms and an unsaturated fatty acid having 16 to 22 carbon atoms.

A solid cosmetic preparation according to the invention comprises a fat and oil composition, called also a plastic fat, comprising (1) a fatty acid moiety having one or more mixed acid triglyceride having one or two straight, saturated C20 to C26, preferably C20 to C24, fatty acid residue and one or two unsaturated C16 to C22 fatty acid residue in a molecule thereof and (2) in the entire fatty acid moiety, 15 to 70 wt. % of one or two saturated C20 to C26, preferably C20 to C24, fatty acids and 20 to 60 wt. % of one or two unsaturated C16 to C22 fatty acids. It is useful as a base of a solid cosmetic preparation.

It is preferred that said composition comprises 30 to 70 wt. %, more preferably 40 to 65 wt. %, of one or more saturated fatty acids having 20 or above, especially 20 to 24, carbon atoms. It is also preferable that the unsaturated fatty acids are contained in an amount of 25 to 50 wt. % in the composition.

A preferable embodiment of the solid cosmetic preparation comprises 0.1 to 80 percent by weight of said composition and 99.9 to 20 percent by weight of one or more conventional cosmetic components.

It is preferred that the composition comprises 35 wt. % or more of the mixed acid triglyceride.

The solid cosmetic preparation of the invention is so oily as to have a good spread and luster and a high flexibility. It also has little liability to change in hardness with a temperature change, but no liability to deteriorate in quality owing to sweating or blooming. The preparation is of the pressed powder type, having an excellent impact resistance and a good feeling in use and developing no shininess.

The solid cosmetic preparation of the invention may further comprise an alpha-mono(methyl-branched alkyl)glyceryl ether of the formula (1)

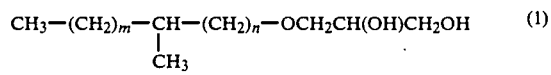

in which m is an integrer of 2 to 14, n is an integer of 3 to 11 and the total of m and n is 9 to 21.

The preparation may further comprise a cholesteryl ester of a branched fatty acid of the formula (2)

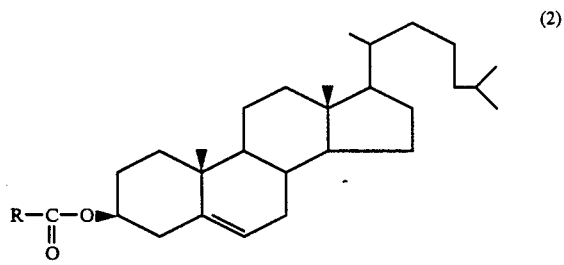

in which R is a saturated aliphatic hydrocarbon group having 11 to 23 carbon atoms and at least one alkyl substituent between the carboxyl-bonded position and the center of the main chain thereof.

According to the invention, the solid cosmetic preparation provides preferable embodiments which further comprise the above shown glyceryl ether (1) and/or the above defined cholesteryl ester (2). The embodiments provide a satisfactory shape retention, feeling in use, finish and wear.

It has been recognized that the plastic fat used in the present invention, when blended in a cosmetic preparation, exerts a remarkable feeling-improving effect including very good spread and soft touch in application thereof to the skin. It has also been found that the finish and wear are improved to some extent, but the improving effect is yet insufficient and unsatisfactory.

Utilization of an α-mono(methyl-branched alkyl)-glyceryl ether in a cosmetic preparation as used in the present invention has already been disclosed in Japanese Patent Laid-Open No. 120,508/1982, which teaches that the utilization prevents deterioration of the appearance quality, reduction in the breaking strength, and worsening of feeling in use caused by sweating and blooming during the storage of a bar-like cosmetic preparation. It has also been found that the finish and wear are improved to some extent, but the improving effect is yet insufficient and unsatisfactory.

The inventors of the present invention have found that blending of the above-mentioned plastic fat together with an α-mono(methyl-branched alkyl)-glyceryl ether in a cosmetic preparation provides a marked synergistic effect.

Specifically, it has been found that such blending can provide a cosmetic preparation dramatically improved in feeling in use, finish and wear without any problem of shape retention, as compared with blending of a single component of them.

It has also been found that the wear can be further improved when a cholesteryl ester of a branched fatty acid is further incorporated into a cosmetic preparation containing a plastic fat and an α-mono(methyl-branched alkyl)glyceryl ether.

The plastic fat to be contained in the cosmetic preparation of the present invention mainly consists of a mixed acid triglyceride of a di-saturated and mono-unsaturated type mainly having two straight-chain saturated acyl groups in the molecule. At least one of the straight-chain saturated acyl groups in the mixed acid triglyceride has 20 or more carbon atoms, preferably 20 to 26 carbon atoms, while the other straight-chain saturated acyl group has 16 or more carbon atoms, preferably 16 or 26 carbon atoms. The unsaturated acyl group has 16 to 22 carbon atoms. Above all, it is preferred that both of the two straight-chain saturated acyl groups have 20 to 26 carbon atoms. The remaining component of the plastic fat is triglycerides comprising, as the constituent fatty acids, straight chain saturated fatty acids having 8 or more carbon atoms and/or unsaturated carbon atoms having 8 or more carbon atoms. The preferred number of carbon atoms in those fatty acids is 16 to 24. Where the number of carbon atoms in the constituent fatty acid is 8 or less, there arise fears of bad smell and skin stimulation caused by hydrolysis. In the present invention, the term "mainly consisting of a mixed acid triglyceride of a saturated fatty acid having 20 or more carbon atoms and an unsaturated fatty acid having 16 to 22 carbon atoms" is intended to mean that it is the most abundant component of triglycerides with a content of the above-mentioned mixed acid triglyceride of the di-saturated and mono-unsaturated type in the plastic fat of usually about 35% or more, preferably 45% or more.

Unsaturated fatty acids with 16 to 22 carbon atoms which can constitute the above-mentioned plastic mixed acid triglyceride include oleic, linolic, and linolenic acids, the bonding position of which may be either an α position or a β position, preferably both of them to provide a mixture. Though the position and number of unsaturated bonds in the unsaturated fatty acids are not limited, the preferred number of the unsaturated bonds is 1 or 2 from the viewpoint of oxidation stability. Usable straight-chain saturated fatty acids with 20 or more carbon atoms include arachic and behenic acids. The especially preferred number of carbon atoms in them is in a range of 20 to 26, out of which slightly poor flexibility may ensue. Where the number of carbon atoms is 18 or less, the crystallinity is apparently high to lead to brittleness, with the result that the above-mentioned performance cannot be exhibited when blended into a solid cosmetic preparation.

The content of the above-mentioned plastic fat in the solid cosmetic preparation of the present invention is different depending on the shape of the preparation, and can be in a range of 0.1 to 80 wt. %, preferably 0.2 to 50 wt. % in usual. When it is below the range, no sufficient effect can be secured. On the other hand, when it is above the range, the effect is saturated only with an economical disadvantage, and the feeling in use is deteriorated with poor spread, etc. due to the appearance of the properties of the plastic fat itself in the cosmetic preparation, to the detriment of the performance of the cosmetic preparation.

The process of preparing the plastic fat to be used in the present invention is not particularly limited. The plastic fat can be obtained according to, for example, the process disclosed in Japanese Patent Laid-Open No. 53,598/1985.

Preferred α-mono(methyl-branched alkyl)-glyceryl ethers represented by the formula (1) to be used in the present invention are those having a sum of m and n of 13 to 17 (namely a total number of carbon atoms in the alkyl group of 16 to 60). More preferred are those having a sum of m and n of 15 (namely a total number of carbon atoms in the alkyl group of 18). The branched methyl group is preferably positioned close to the center of the main alkyl chain.

The content of the above-mentioned α-mono(methyl-branched alkyl)glyceryl ether in the solid cosmetic preparation is different depending on the shape of the preparation, and can be in a range of 0.1 to 10 wt. %, preferably 0.5 to 8 wt. When it is below the range, no sufficient effect can be secured. On the other hand, when it is above the range, an influence on the physical properties of the fat appears, and there may arise a problem of shape retention, including a decreased breaking strength, for example, in the case of lipsticks.

A process of preparing an α-mono(methyl-branched alkyl)glyceryl ether to be used in the present invention is disclosed in Japanese Patent Laid-Open No. 133,281/1981. However, the process of preparing an α-mono(methyl-branched alkyl)glyceryl ether to be used in the present invention is not limited to this.

Branched fatty acids (RCOOH) to be used in the preparation of the cholesteryl ester of the branched fatty acid that may be used in the present invention include those having 12 to 24 carbon atoms (11 to 23 carbon atoms in R). Preferred are those having 14 to 20 (13 to 19 carbon atoms in R).

The branched fatty acid is a saturated one having at least one alkyl substituent between the carboxyl group-bonded position and the center of the main chain. Such branched saturated fatty acids are easily obtained from raw materials in the petrochemical and fat industries.

Such branched saturated fatty acids obtained from raw materials in the petrochemical industry include those having a side chain at the α position and represented by the following formula:

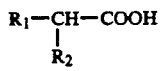

(wherein $R_1$ and $R_2$ are each a straight-chain or branched saturated aliphatic hydrocarbon group, and the sum of carbon atoms in $R_1$ and $R_2$ is 12 to 18).

Specific preferred examples of branched saturated fatty acids having a side chain at the α position include 5,7,7-trimethyl-2-(1,3,3-trimethylbutyl)octanoic, 2-heptylundecanoic, 2-hexyldecanoic, 2-octyldodecanoic and 2-pentylnonanoic acids.

Branched saturated fatty acids obtained from raw materials in the fat industry include those having a branched methyl chain and represented by the following formula:

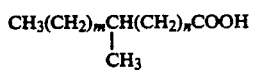

(wherein the sum of m and n is 14 and has a distribution with a center of m=n=7).

An example of such methyl-branched fatty acids is methyl-branched isostearic acid obtained as a by-product in the production of a dimer of oleic acid. For example, its isopropyl ester is commercially available (Emery Industries, Inc., USA, etc.).

The cholesteryl ester of the branched fatty acid that may be contained in the cosmetic preparation of the present invention is prepared from the above-mentioned branched fatty acid or a derivative thereof and cholesterol according to a customary ester preparation process.

The content of the above-mentioned cholesteryl ester of the branched fatty acid in the solid cosmetic preparation is different depending on the shape of the preparation, and can be in a range of 0.01 to 50 wt. %, preferably 0.03 to 30 wt. % in usual. When it is below the range, no sufficient effect can be secured. On the other hand, when it is above the range, the effect is saturated only with an economical disadvantage, and problems including appearance of stickiness are liable to arise due to the appearance of the properties of the cholesteryl ester of the branched fatty acid itself.

A process of preparing the cholesteryl ester of the branched fatty acid that may be used in the present invention is disclosed in Japanese Patent Laid-Open No. 65,900/1981. However, the process of preparing the cholesteryl ester of the branched fatty acid is not limited to this.

The production of the solid cosmetic preparation of the present invention (bar-like cosmetic preparation) is conducted according to a customary process except for incorporation of the abovementioned components in respective blending amounts into the formulation of the cosmetic preparation. Specifically, the above-mentioned amounts of the plastic fat, the α-mono(methyl-branched alkyl)-glyceryl ether, and the cholesteryl ester of the branched fatty acid, as well as oily base materials such as fat or oil and wax are molten by heat, and admixed with an arbitrary component such as a pigment, a perfume, or a pharmaceutical ingredient according to need until homogeneity is attained. The obtained mixture is cast into a mold, and cooled to be solidified and formed into a bar-like product.

Oily base materials that can be used in the present invention include solid or semi-solid oily base materials such as carnauba wax, candelilla wax, rice wax, Japan wax, beeswax, ceresin wax, microcrystalline wax, paraffin wax, hardened tallow, hardened castor oil, hardened jojoba oil, lanolin, and vaseline; and liquid oily base materials such as liquid paraffin, squalane, olive oil, castor oil, jojoba oil, silicone oil, and synthetic ester oils. In addition, solid paraffin, beeswax, cacao butter, an aliphatic acid and a higher alcohol may be used.

Arbitrary components may be employed without any limitation. Typical components include coloring materials such as inorganic pigments including iron oxide and titanium oxide, and lake pigments; various oily pharmaceutical ingredients such as anti-oxidizing agents, anti-phlogistic agents, vitamins, and antibacterial agents; and talc, kaolin, metallic soaps, mica powder, sericite, and nylon powder.

Cosmetic preparations obtained in such a way include all types of bar-like solid or semi-solid cosmetic preparations such as lipsticks, lip cream, stick eye shadow, cosmetic pencils, and stick pomade.

BRIEF DESCRIPTION OF THE DRAWINGS

The drawing is a graph showing variation of breaking strength with the storage temperature for various lip creams obtained in Example 1.

EXAMPLES

Figure 1:
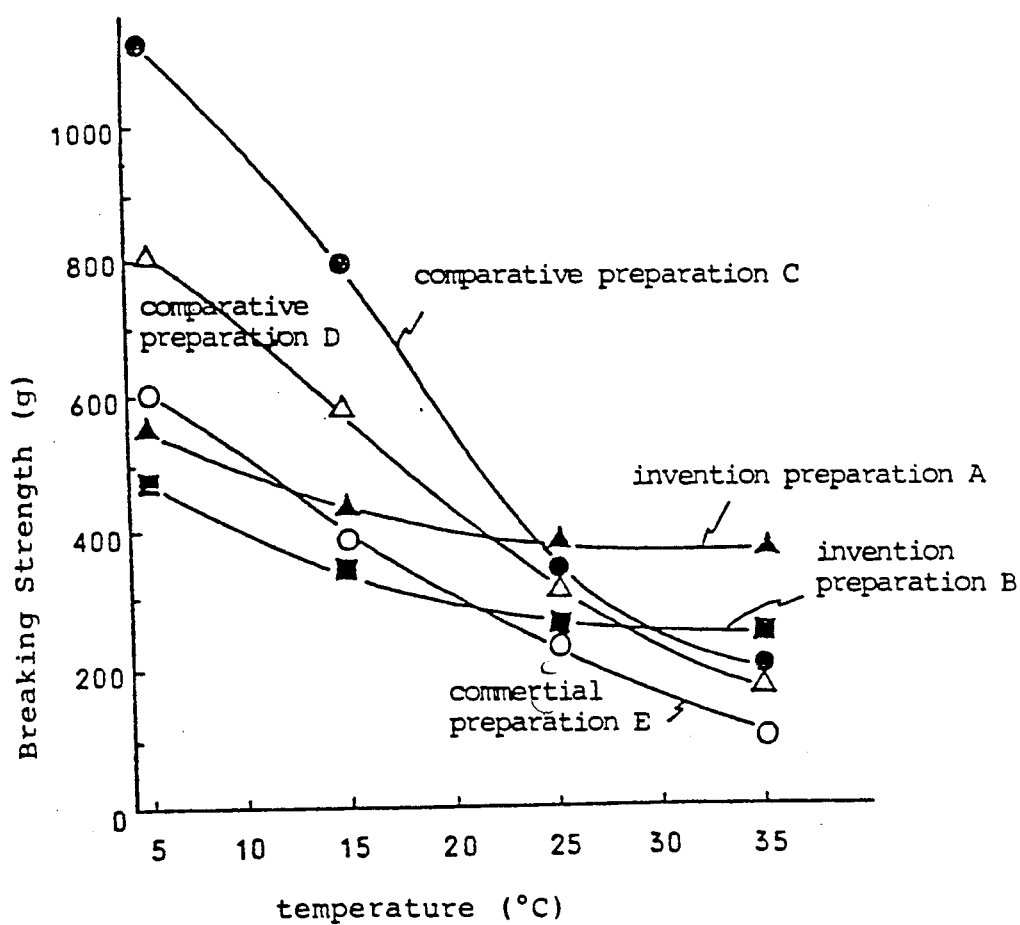

The following Synthesis Examples and Examples will illustrate the present invention in more detail, but they should not be construed as limiting the scope of the invention. All "%" and "part(s)" in these Examples are by weight.

SYNTHESIS EXAMPLE 1

50 wt. % of olive oil and 50 wt. % of behenic acid were dissolved in hexane in a volume of 5 times the weight of the fatty acids. 520 lipase units, per g of the feed, of 10 wt. % lipase adsorbed on celite and having a capacity of selective ester exchange at the α position (lipase of Rhizopus delemar manufactured by Tanabe Seiyaku Co., Ltd.) was added thereto. Then, an α-position-selective ester exchange reaction was conducted at 45° C. for 72 hours. After the reaction, the reaction mixture was filtered, followed by distilling off hexane from the filtrate. Subsequently, the fatty acids were removed from the residue by molecular distillation. The α-position-selectively ester-exchanged oil from which the fatty acids were removed was dissolved in acetone in an amount of 5 ml per g of the oil, followed by cooling from 30° C. to 10° C. with stirring. Precipitated crystals were removed, and the solvent was distilled off. Thereafter, deodorizing was effected according to a customary method. Thus Plastic Triglyceride a was obtained.

SYNTHESIS EXAMPLE 2

A mixed oil composed of 50 wt. % of triglyceride of behenic acid and 50 wt. % of safflower oil was reacted in the presence of a sodium methylate catalyst in an amount of 0.1 wt. % based on the oil at 80° C. for 30 minutes to obtain an ester-exchanged oil. This ester-exchanged oil was dissolved in n-hexane in an amount of 4 ml per g of the oil, followed by cooling from 40° C. to 28° C. with stirring. The precipitated high-melting part mainly composed of a trisaturated triglyceride (yield: 14% based on the ester-exchanged oil) was filtered off. The solvent was distilled off from the filtrate according to a customary method. The residue was dissolved in acetone in an amount of 5 ml per g of the residue, followed by cooling from 30° C. to 10° C. with stirring. The precipitated desired fraction was collected.

The solvent was distilled off from the fraction. Deodorizing was effected according to a customary method. Thus Plastic Triglyceride b was obtained.

SYNTHESIS EXAMPLE 3

A mixed oil composed of 50 wt. % of a triglyceride of a high-boiling fraction of an extremely hardened fish oil fatty acid as the raw material and 50 wt. % of safflower oil was reacted in the presence of a sodium methylate catalyst in an amount of 0.1 wt. % based on the oil at 80° C. for 30 minutes to obtain an ester-exchanged oil. This oil was dissolved in acetone in an amount of 5 ml per g of the oil at 60° C., followed by cooling to 25° C. with stirring. The precipitated high-melting part mainly composed of a trisaturated triglyceride (yield: 15% based on the ester-exchanged oil) was removed. The filtrate was cooled to 3° to 5° C. with stirring. The precipitated desired fraction (medium-melting fraction) was collected.

The solvent was distilled off from the fraction. Deodorizing was effected according to a customary method. Thus Plastic Triglyceride c was obtained.

SYNTHESIS EXAMPLE 4

A mixed oil composed of 50 wt. % of an extremely hardened high-erucin rapeseed oil and 50 wt. % of safflower oil was subjected to the same ester exchange as in Synthesis Example 2. The obtained ester-exchanged oil was dissolved in acetone in an amount of 5 ml per g of the oil at 60° C., followed by cooling to 35° C. with stirring. The precipitated high-melting part mainly composed of a trisaturated triglyceride (yield: 26% based on the ester-exchanged oil) was filtered off. The filtrate was cooled to 10° C. with stirring. The precipitated crystals were collected. The solvent was distilled off from the fraction. Deodorizing was effected according to a customary method. Thus Plastic Triglyceride d was obtained.

SYNTHESIS EXAMPLE 5

A mixed oil composed of 50 wt. % of triglyceride of behenic acid and 50 wt. % of olive oil was subjected to the same ester exchange as in Synthesis Example 2, followed by solvent fractionation. Thus desired Plastic Triglyceride e was obtained.

Analysis values for Plastic Triglycerides a to e obtained in Synthesis Examples 1 to 5 are listed in Table 1. The compositions of the triglycerides as determined by gas chromatography are listed in Table 2.

TABLE 1

|  | (Note 1) Yield (%) | Iodine No. | Melting point (°C.) | Fatty acid composition (%) | | | | | | | |
|---|---|---|---|---|---|---|---|---|---|---|---|
|  |  |  |  | $C_{16}$ | $C_{18}$ | $C_{18=1}$ | $C_{18=2}$ | $C_{18=3}$ | $C_{20}$ | $C_{22}$ | $C_{24}$ |
| Plastic Triglyceride a | 68.5 | 32.0 | 44.3 | 3.7 | 2.9 | 32.4 | 1.9 | 0.8 | 5.0 | 52.0 | 1.6 |
| Plastic Triglyceride b | 46.9 | 56.8 | 41.9 | 3.7 | 2.4 | 4.9 | 29.8 | 0.1 | 3.2 | 53.9 | 2.0 |
| Plastic Triglyceride c | 43.6 | 58.2 | 41.8 | 1.2 | 6.5 | 5.7 | 29.3 | — | 29.1 | 27.9 | — |
| Plastic Triglyceride d | 32.6 | 53.7 | 42.1 | 4.3 | 17.3 | 3.7 | 28.6 | 0.1 | 6.8 | 38.8 | 1.4 |
| Plastic Triglyceride e | 43.7 | 32.5 | 43.2 | 4.5 | 2.4 | 28.2 | 3.8 | 0.3 | 4.7 | 53.4 | 2.0 |

Note 1; Yield based on ester-exchanged oil

TABLE 2

|  | Triglyceride composition (%)* | | | | | | |
|---|---|---|---|---|---|---|---|
|  | $C_{52}$ | $C_{54}$ | $C_{56}$ | $C_{58}$ | $C_{60}$ | $C_{62}$ | $C_{64}$ |
| Plastic Triglyceride a | 1.2 | 4.2 | 13.9 | 25.2 | 10.2 | 41.1 | 1.8 |
| Plastic Triglyceride b | 0.8 | 2.4 | 7.8 | 28.8 | 11.9 | 47.5 | 0.9 |
| Plastic Triglyceride c | 1.0 | 3.5 | 15.6 | 32.0 | 32.3 | 15.5 | — |
| Plastic Triglyceride d | 2.6 | 9.2 | 7.2 | 34.7 | 7.6 | 38.3 | 0.4 |
| Plastic Triglyceride e | 0.5 | 2.5 | 9.6 | 24.6 | 12.2 | 42.1 | 2.6 |

(Note)
*The main component(s) is PSU for $C_{52}$, $S_2U$ for $C_{54}$, ASU for $C_{56}$, AAU and BSU for $C_{58}$, ABU for $C_{60}$, $B_2U$ for $C_{62}$, and $B_2A$ for $C_{64}$, wherein P stands for palmitic acid, S for stearic acid, U for $C_{18}$ unsaturated acid, A for arachic acid, and B for behenic acid.

EXAMPLE 1

Lip cream

Components as shown in Table 3 were heated at 80° C. and homogeneously mixed, cast into a mold, and cooled to be solidified for preparing a lip cream. As to each of lip creams A to D thus prepared and a commercially available lip cream E (fluid polyisobutylene: 32%, castor oil and wax: 64%, others: pigment, etc.), the breaking strength at each temperature was examined according to the measurement method as described below. The results are shown in the drawing. Organoleptic evaluation of feeling in use thereof was conducted by 20 common women. The results are shown in Table 4.

TABLE 3

|  | Specimen code | | | |
|---|---|---|---|---|
|  | Present invention | | Comparative | |
| Composition | A | B | C | D |
| carnauba wax | 5 parts | 5 | 5 | 5 |
| ceresin | 10 | 10 | 10 | 10 |
| candelilla wax | 4 | 4 | 4 | 4 |
| beeswax | — | — | — | 10 |
| hardened palm oil | — | — | 10 | — |
| Plastic Triglyceride a | 10 | — | — | — |
| Plastic Triglyceride b | — | 10 | — | — |
| lanolin | 12 | 12 |  |  |
| castor oil | 20 | 20 | 20 | 20 |
| olive oil | 39 | 39 | 39 | 39 |
| anti-oxidizing agent | adequate amount | adequate amount | adequate amount | adequate amount |
| perfume | adequate amount | adequate amount | adequate amount | adequate amount |

Breaking Strength Measurement Method

The preparations A and B of this invention and the comparative preparations C and D as shown in Table 3 which were each molded into a cylinder of 11 mm in diameter, and a commercially available lip cream E as a comparative preparation were kept at each temperature, and examined as to breaking strength by using a rheometer (NRM-20105 manufactured by Fudow Chemical Co., Ltd.). Measurement was made by applying a vertical stress on a position 10 mm apart from a fixed site at a rate of 100 mm/sec. The maximum stress till the stick was broken was recorded, and regarded as the breaking strength.

As is apparent from the drawing, variation of breaking strength with the temperature is smaller for the preparations according to the present invention than for the comparative preparations.

TABLE 4

Organoleptic Evaluation Results

| Formulation | Spread | Smoothness | Non-stickiness |
|---|---|---|---|
| A of present invention | ⊚ | ○ | ○ |
| B of present invention | ⊚ | ⊚ | ⊚ |
| Comparative C | ○ | ○ | x |
| Comparative D | Δ | ○ | x |
| Commercially available E | Δ | ○ | ○ |

(Note) Evaluation Standard
⊚: at least 16 women judged as good.
○: 12 to 15 women judged as good.
Δ: 8 to 11 women judged as good.
x: at most 7 women judged as good.

EXAMPLE 2

Lipstick

Lipsticks having compositions as shown in Table 5 were prepared, and evaluated as to performance by 10 professional panelists.

The results are shown in Table 6.

TABLE 5

| | Specimen code | | | | |
|---|---|---|---|---|---|
| | Present invention | | | | Comparative |
| Composition | F | G | H | I | J |
| carnauba wax | 2 parts | 2 | 2 | 2 | 2 |
| ceresin | 4 | 4 | 4 | 4 | 4 |
| candelilla wax | 5 | 5 | 5 | 5 | 5 |
| microcrystalline wax | 2 | 2 | 2 | 2 | 2 |
| beeswax | 5 | 5 | 5 | 5 | 5 |
| lanolin | 4 | 4 | 4 | 4 | 4 |
| castor oil | 45 | 45 | 40 | 35 | 45 |
| hexadecyl alcohol | 24 | 20 | 20 | 15 | 25 |
| Plastic Triglyceride c | 1 | — | — | 10 | — |
| Plastic Triglyceride d | — | 4 | — | — | — |
| Plastic Triglyceride e | — | — | 10 | 10 | — |
| titanium oxide | 2 | 2 | 2 | 2 | 2 |
| pigment (Red No. 202) | 2 | 2 | 2 | 2 | 2 |
| pigment (Red No. 204) | 1 | 1 | 1 | 1 | 1 |
| pigment (Yellow No. 4 Al lake) | 3 | 3 | 3 | 3 | 3 |
| anti-oxidizing agent | adequate amount | ← | ← | ← | ← |
| perfume | adequate amount | ← | ← | ← | ← |

TABLE 6

| | Specimen code | | | | |
|---|---|---|---|---|---|
| | Present invention | | | | Comparative |
| Evaluation | F | G | H | I | J |
| Luster of stick | ○ | ⊚ | ⊚ | ○ | Δ |
| Spread | ○ | ⊚ | ⊚ | ○ | Δ |
| Bonding | ○ | ○ | ⊚ | ○ | ○ |
| Smoothness | ○ | ⊚ | ⊚ | ○ | ○ |
| Luster in application | ⊚ | ⊚ | ⊚ | ○ | ○ |

(Note) Evaluation Standard
⊚: at least 8 of 10 panel lists estimated as good.
○: at least 6 of 10 panel lists estimated as good.
Δ: at least 4 of 10 panel lists estimated as good.
x: at most 3 of 10 panel lists estimated as good.

These results indicate that the preparations according to the present invention are excellent in luster of stick, spreadability, smoothness and luster in their use.

EXAMPLE 3

Specimens of the lip creams as shown in Tables 3 and 5, and the lipsticks A, B, G, and H of the present invention and comparative lipsticks C, D, and J as shown in Table 7 were examined as to occurrence or non-occurrence of sweating or blooming. The occurrence of sweating was judged by visually observing the state of sweating after a specimen was allowed to stand at 5° C. for 4 hours and at 35° C. at 60 RH for 4 hours, while that of blooming was judged by visually observing the state of a specimen after it was allowed to stand at 35° C. for 8 hours and at 5° C. for 24 hours. The results are shown in Table 7.

TABLE 7

| Specimen | Specimen code | Sweating | Blooming |
|---|---|---|---|
| Lip cream | | | |
| Present invention | A | — | — |
| | B | — | — |
| Comparative | C | ++ | +++ |
| | D | + | + |
| Lipstick | | | |
| Present invention | G | — | — |
| | H | — | — |
| Comparative | J | + | + |

(Note) Evaluation Standard
—: not observed at all
+: slightly observed
++: observed
+++: considerably observed Neither sweating nor blooming was observed in the preparations of the present invention, which were found to be quite stable in quality.

EXAMPLE 4

Eyebrow pencil

Eyebrow pencils having compositions as shown in Table 8 were prepared according to the method as described below. Evaluation of feeling in their use was conducted by 10 professional panelists. The results are shown in Table 9.

TABLE 8

| | Specimen code | |
|---|---|---|
| | Present invention | Comparative |
| Composition | K | L |
| Japan wax | 5 parts | 15 |
| hardened tallow | 5 | 10 |
| beeswax | 5 | 5 |

TABLE 8-continued

| | Specimen code | |
|---|---|---|
| Composition | Present invention K | Comparative L |
| Plastic Triglyceride a | 15 | — |
| paraffin | 5 | 5 |
| stearic acid | 15 | 15 |
| black iron oxide | 30 | 30 |
| red iron oxide | 10 | 10 |
| titanium oxide | 10 | 10 |

Preparation Method

Components were heated at 80° C. and repeatedly kneaded with a roll mill. The kneaded mass was cooled to room temperature and extruded into a core from a nozzle with a compression injection machine. The core was mounted on a wooden part having a groove with a core shape, followed by bonding, combining, and cutting. Thus a pencil-shaped product was prepared.

TABLE 9

| | Specimen code | |
|---|---|---|
| Evaluation item | Present invention K | Comparative L |
| Easiness in drawing | 9 | 1 |
| Softness | 6 | 4 |
| Smoothness | 8 | 2 |

(Note)
The figures in the Table represent the number of panelists who positively answered in a comparison of both.

In the case of pencil-type cosmetic preparations, the hardness and smoothness of a core can be controlled by the ratio of the wax to the oil components. In general, however, use of a low-melting wax provides a soft core without gritty touch, but is liable to cause poor smoothness because of its viscosity. This liability can be moderated to some extent by the use of a triglyceride of a straight-chain saturated fatty acid having a sharp melting point around the body temperature. However, this effect is not sufficient.

Blending of a plastic mixed acid triglyceride can provide a pencil-type cosmetic preparation having soft touch and excellent smoothness, as is understood from Table 9.

EXAMPLE 5

Solid powder eye shadow

Solid powder eye shadows having compositions as shown in Table 10 were prepared according to the method as described below, and evaluated as to the physical properties and feeling in their use. The results are summarized in Table 11.

TABLE 10

| | Specimen code | | | |
|---|---|---|---|---|
| | Present invention | | Comparative | |
| Composition | M | N | O | P |
| talc | 20 parts | 15 | 15 | 15 |
| sericite | 10 | 30 | 30 | 30 |
| micaceous titanium | 50 | 35 | 35 | 35 |
| ultramarine | 5 | 5 | 5 | 5 |
| iron oxide | 1 | 2 | 2 | 2 |
| squalane | 10 | 10 | 10 | 0 |
| lanolin | — | — | — | 2 |
| hardened palm oil | — | — | 2 | — |
| Plastic Triglyceride a | 2 | — | — | — |
| Plastic Triglyceride e | — | 2 | — | — |
| paraffin | 2 | 1 | 1 | 1 |

Preparation Method

Powdery components were stirred and mixed, and sprayed with oily components which were heated and homogeneously dissolved, followed by further stirring. Thereafter, the resulting mixture was pulverized and compression-molded with a molding machine to obtain a solid powder eye shadow.

TABLE 11

| | Present invention | | Comparative | |
|---|---|---|---|---|
| | M | N | O | P |
| Impact resistance | O | O | x | Δ |
| Falling off | O | O | Δ | Δ |
| Appearance (shininess) | O | O | O | x |
| Bonding | O | O | x | Δ |
| Easiness in gradation | O | O | Δ | x |

Evaluation of Impact Resistance 10 pieces of a solid powder eye shadow containers in aluminum dish-like containers were dropped on an iron plate from a height of 1 m. Thereafter, they were observed for breakage, cracking, and chipping.

⊚: none of 10 pieces underwent changes such as breakage, cracking, or chipping.
O: at most 4 of 10 pieces underwent cracking or chipping.
Δ: at least 5 of 10 pieces underwent cracking or chipping.
x: at least 5 of 10 pieces underwent breakage into pieces.

Evaluation of Falling Off

The surface of an eye shadow was rubbed with a make-up tip therefor to evaluate falling off.
: well (uniformly) fell off
Δ: partially formed into lumps
x: hardly fell off with many lumps

Evaluation of Appearance, Bonding, and Easiness in Gradation

Evaluation of appearance, bonding, and easiness in gradation in their use was conducted by 10 professional panelists.
: at least 7 panelists judged as good.
Δ: 4 to 6 panelists judged as good.
x: at most 3 panelists judged as good.

The preparations according to the present invention containing a plastic triglyceride not only had high impact resistances but also were good in falling off and bonding. They showed no shininess. Thus, they exhibited excellent performances.

EXAMPLE 6

Lipstick

Components listed in Table 12 were heated at 80° C. and homogeneously mixed, cast into a mold, and cooled to be solidified to prepare lipsticks. The performance evaluation of them was conducted by 10 professional panelists.

Results are shown in Table 13.

These results show that the preparations according to the present invention are excellent in shape retention, feeling in use (spread, bonding, and smoothness), finish (stickiness and fit), and wear (color fading and blurring resistance).

TABLE 12

| Composition | Specimen code | | | | | | | |
|---|---|---|---|---|---|---|---|---|
| | Present invention | | | | Comparative | | | |
| | L-1 | L-2 | L-3 | L-4 | L-5 | L-6 | L-7 | L-7 |
| carnauba wax | 2 parts | 2 | 2 | 2 | 2 | 2 | 2 | 2 |
| ceresin | 4 | 4 | 4 | 4 | 4 | 4 | 4 | 4 |
| candelilla wax | 5 | 5 | 5 | 5 | 5 | 5 | 5 | 5 |
| microcrystalline wax | 2 | 2 | 2 | 2 | 2 | 2 | 2 | 2 |
| beeswax | 5 | 5 | 5 | 5 | 5 | 5 | 5 | 5 |
| hardened palm oil | 4 | — | 4 | — | 5 | 4 | — | 5 |
| lanolin | 5 | 5 | 3 | — | 5 | 5 | 5 | 5 |
| castor oil | 39 | 38 | 39 | 38 | 40 | 40 | 40 | 38 |
| hexadecyol alcohol | 24 | 24 | 24 | 24 | 24 | 24 | 24 | 24 |
| plastic fat*1 | 1 | 5 | 1 | 5 | — | 1 | 5 | — |
| α-mono(methyl-branched alkyl)-glyceryl ether*2 | 1 | 2 | 1 | 2 | — | — | — | 2 |
| cholesteryl ester of branched fatty acid*3 | — | — | 2 | 5 | — | — | — | — |
| titanium oxide | 2 | 2 | 2 | 2 | 2 | 2 | 2 | 2 |
| pigment (Red No. 202) | 2 | 2 | 2 | 2 | 2 | 2 | 2 | 2 |
| pigment (Red No. 204) | 1 | 1 | 1 | 1 | 1 | 1 | 1 | 1 |
| pigment (Yellow No. 4 Al lake) | 3 | 3 | 3 | 3 | 3 | 3 | 3 | 3 |
| anti-oxidizing agent | adequate amount | adequate amount | adequate amount | adequate amount | adequate amount | adequate amount | adequate amount | adequate amount |
| perfume | adequate amount | adequate amount | adequate amount | adequate amount | adequate amount | adequate amount | adequate amount | adequate amount |

(Note)
*1 Plastic fat obtained according to the following synthesis method.
A mixed oil composed of 50 wt. % of triglyceride of behenic acid and 50 wt. % of safflower oil was reacted in the presence of a sodium methylate catalyst in an amount of 0.1 wt. % based on the oil at 80° C. for 30 minutes to obtain an ester-exchanged oil. This ester-exchanged oil was dissolved in n-hexane in an amount of 4 ml per g of the oil, followed by cooling from 40° C. to 28° C. with stirring. The precipitated high-melting part mainly composed of a trisaturated (yield: 14% based on the ester-exchanged oil) was filtered off. The solvent was distilled off from the filtrate according to a customary method. The residue was dissolved in acetone in an amount of 5 ml per g of the residue, followed by cooling from 30° C. to 10° C. with stirring. The precipitated desired fraction was collected.
The solvent was distilled off from the fraction. Deodorizing was effected according to a customary method. Thus a plactic fat was obtained.
*2 α-Mono(isostearyl)glyceryl ether prepared from Emery 2310 isopropyl isostearate (manufactured by Emery Industries, Inc., USA) and isopropylidene glycerol.
*3 Cholesteryl ester of a branched fatty acid prepared from Emery 875 isostearic acid (manufactured by Emery Industries, Inc., USA) and cholesterol.

TABLE 13

| Test item | Specimen code | | | | | | | |
|---|---|---|---|---|---|---|---|---|
| | Present invention | | | | Comparative | | | |
| | L-1 | L-2 | L-3 | L-4 | L-5 | L-6 | L-7 | L-8 |
| Shape retention | ⊚ | ⊚ | ⊚ | ⊚ | ○ | ⊚ | ⊚ | ⊚ |
| | ⊚ | ⊚ | ⊚ | ⊚ | ○ | ⊚ | ⊚ | ○ |
| Spreadability | ⊚ | ⊚ | ⊚ | ⊚ | △ | ○ | ○ | △ |
| Bonding | ⊚ | ⊚ | ⊚ | ⊚ | △ | △ | ⊚ | △ |
| Smoothness | ⊚ | ⊚ | ⊚ | ⊚ | × | ○ | ○ | △ |
| Non-stickiness | ⊚ | ⊚ | ⊚ | ⊚ | △ | △ | ○ | ○ |
| | ⊚ | ⊚ | ⊚ | ⊚ | ○ | ○ | ○ | ○ |
| Fit | ⊚ | ⊚ | ⊚ | ⊚ | △ | △ | ○ | △ |
| Color fading | ⊚ | ⊚ | ⊚ | ⊚ | × | × | △ | △ |
| Blur resistance | ○ | ○ | ⊚ | ⊚ | × | × | △ | △ |
| | ○ | ○ | ⊚ | ⊚ | ○ | ○ | ○ | ○ |

(Note) Evaluation Standard
⊚: at least 8 of 10 panelists gave good evaluation.
○: at least 6 of 10 panelists gave good evaluation.
△: at least 4 of 10 panelists gave good evaluation.
×: at most 3 of 10 panelists gave good evaluation.

EXAMPLE 7

Eyebrow Pencil

Eyebrow pencils having compositions as shown in Table 14 were prepared according to the method as described below. The performance evaluation of them was conducted by 10 professional panelists.

Results are shown in Table 15.

Preparation Method

Components were heated at 80° C. and repeatedly kneaded with a roll mill. The kneaded mass was cooled to room temperature and extruded into a core from a nozzle with a compression injection machine. The core was mounted on a wooden part having a groove with a core shape, followed by bonding, combining, and cutting. Thus a pencil-shaped product was prepared.

TABLE 14

| Composition | Specimen code | | | | | | | |
|---|---|---|---|---|---|---|---|---|
| | Present invention | | | | Comparative | | | |
| | I-1 | I-2 | I-3 | I-4 | I-5 | I-6 | I-7 | I-8 |
| Japan wax | 10 parts | 6 | 10 | 6 | 12 | 11 | 7 | 11 |
| hardened tallow | 9 | 4 | 9 | 4 | 10 | 9 | 5 | 9 |
| beeswax | 5 | 5 | 5 | 5 | 5 | 5 | 5 | 5 |
| paraffin | 5 | 5 | 5 | 6 | 5 | 5 | 5 | 5 |
| stearic acid | 15 | 15 | 15 | 15 | 15 | 15 | 15 | 15 |
| lanolin | 3 | 3 | 2 | — | 3 | 3 | 3 | 3 |
| plastic fat | 2 | 10 | 2 | 10 | — | 2 | 10 | — |
| α-mono(methyl-branched alkyl)-glyceryl ether | 1 | 2 | 1 | 2 | — | — | — | 2 |
| cholesteryl ester of branched | — | — | 1 | 3 | — | — | — | — |

TABLE 14-continued

| Composition | Specimen code | | | | | | | |
|---|---|---|---|---|---|---|---|---|
| | Present invention | | | | Comparative | | | |
| | I-1 | I-2 | I-3 | I-4 | I-5 | I-6 | I-7 | I-8 |
| fatty acid | | | | | | | | |
| black iron oxide | 30 | 30 | 30 | 30 | 30 | 30 | 30 | 30 |
| red iron oxide | 10 | 10 | 10 | 10 | 10 | 10 | 10 | 10 |
| titanium oxide | 10 | 10 | 10 | 10 | 10 | 10 | 10 | 10 |

TABLE 15

| Test item | Specimen code | | | | | | | |
|---|---|---|---|---|---|---|---|---|
| | Present invention | | | | Comparative | | | |
| | I-1 | I-2 | I-3 | I-4 | I-5 | I-6 | I-7 | I-8 |
| Shape retention | ● | ● | ● | ● | ○ | ● | ● | ● |
| Easiness in drawing | ● | ● | ● | ● | Δ | ○ | ● | Δ |
| Softness | ● | ● | ● | ● | Δ | ○ | ○ | Δ |
| Smoothness | ● | ● | ● | ● | Δ | ○ | ● | Δ |
| Unevenness | ● | ● | ● | ● | × | × | Δ | ○ |
| Wear | ○ | ○ | ● | ● | Δ | Δ | ○ | Δ |

(Note) Evaluation Standard
●: at least 8 of 10 panelists gave good evaluation.
○: at least 6 of 10 panelists gave good evaluation.
Δ: at least 4 of 10 panelists gave good evaluation.
×: at most 3 of 10 panelists gave good evaluation.

These results show that the preparations according to the present invention are excellent in feeling in use (spread, bonding, and smoothness) and wear (color fading and blurring resistance).

EXAMPLE 8

Solid Powder Eye Shadow

Solid powder eye shadows having compositions as shown in Table 16 were prepared according to the method as described below. The impact resistance evaluation of them as well as the performance evaluation of them by 10 professional panelists was conducted.

Results are shown in Table 17.

Preparation Method

Powdery components were stirred and mixed, and sprayed with oily components which were heated and homogeneously dissolved, followed by further stirring. Thereafter, the resulting mixture was pulverized and compression-molded with a molding machine to obtain a solid powder eye shadow.

TABLE 16

| Composition | Specimen code | | | | | | | |
|---|---|---|---|---|---|---|---|---|
| | Present invention | | | | Comparative | | | |
| | P-1 | P-2 | P-3 | P-4 | P-5 | P-6 | P-7 | P-8 |
| talc | 15 parts | 15 | 15 | 15 | 15 | 15 | 15 | 15 |
| sericite | 30 | 30 | 30 | 30 | 30 | 30 | 30 | 30 |
| micaceous titanium | 35 | 35 | 35 | 35 | 35 | 35 | 35 | 35 |
| ultramarine | 5 | 5 | 5 | 5 | 5 | 5 | 5 | 5 |
| iron oxide | 2 | 2 | 2 | 2 | 2 | 2 | 2 | 2 |
| squalane | 8 | 8 | 8 | 8 | 8 | 8 | 8 | 8 |
| hardened palm oil | 1.5 | — | 1.5 | — | 2 | 1.5 | — | — |
| lanolin | 2 | 2 | 1.5 | — | 2 | — | — | — |
| paraffin | 0.5 | — | 0.5 | — | 1 | — | — | — |
| plastic fat | 0.5 | 2 | 0.5 | 2 | — | 0.5 | 2 | — |
| α-mono(methyl-branched alkyl)-glyceryl ether | 0.5 | 1 | 0.5 | 1 | — | — | — | 1 |
| cholesteryl ester of branched fatty acid | — | — | 0.5 | 2 | — | — | — | — |

TABLE 17

| Test item | Specimen code | | | | | | | |
|---|---|---|---|---|---|---|---|---|
| | Present invention | | | | Comparative | | | |
| | P-1 | P-2 | P-3 | P-4 | P-5 | P-6 | P-7 | P-8 |
| Impact resistance | ● | ● | ● | ○ | ○ | ● | ● | ● |
| Spreadability | ● | ● | ● | ● | Δ | ● | ● | Δ |
| Bonding | ● | ● | ● | ● | Δ | ● | ○ | Δ |
| Easiness in gradation | ● | ● | ● | ● | Δ | Δ | ○ | Δ |
| Appearance (shininess) | ● | ● | ● | ● | Δ | Δ | ○ | ○ |
| Color development | ● | ● | ● | ● | × | Δ | ○ | ○ |
| Kink | ○ | ○ | ● | ● | × | × | Δ | ○ |
| Falling off | ○ | ○ | ● | ● | × | × | Δ | Δ |

Evaluation of Impact Resistance 10 pieces of a solid powder eye shadow contained in aluminum dish-like containers were dropped on an iron plate from a height of 1 m. Therefore, they were observed for breakage, cracking, and chipping.

◎: None of 10 pieces change without breakage, cracking, or chipping.
○: Not more than 4 of 10 pieces underwent cracking or chipping.
Δ: 5 or more of 10 pieces underwent cracking or chipping.
x: 5 or more of 10 pieces underwent breakage into pieces.

(Organoleptic Evaluation: Spreadability—Falling Off)

◎: at least 8 of 10 panelists gave good evaluation.
○: at least 6 of 10 panelists gave good evaluation.
Δ: at least 4 of 10 panelists gave good evaluation.
x: at most 3 of 10 panelists gave good evaluation.

These results show that the preparations according to the present invention are excellent in shape retention (impact resistance), feeling in use (spreadability, bonding, and easiness in gradation), finish (appearance and color development), and wear (kink and falling off).

EXAMPLE 9

Lip Stick

Components listed in Table 18 were heated at 80° C. and homogeneously mixed, cast into a mold, and cooled to be solidified to prepare lipsticks. The performance evaluation of them was conducted by 10 professional panelists.

Results are shown in Table 19.

TABLE 18

| Composition | Specimen code | | | | | |
|---|---|---|---|---|---|---|
| | Present invention | | | Comparative | | |
| | L-1 | L-2 | L-3 | L-4 | L-5 | L-6 |
| carnauba wax | 2 parts | 2 | 2 | 2 | 2 | 2 |
| ceresin | 4 | 4 | 4 | 4 | 4 | 4 |
| candelilla wax | 5 | 5 | 5 | 5 | 5 | 5 |
| microcrystalline wax | 2 | 2 | 2 | 2 | 2 | 2 |
| beeswax | 5 | 5 | 5 | 5 | 5 | 5 |
| hardened palm oil | 5.5 | 2 | — | 5 | 5 | — |
| lanolin | 3.5 | 1 | — | 5 | — | 5 |
| castor oil | 40 | 40 | 30 | 40 | 40 | 40 |
| hexadecyl alcohol | 24 | 24 | 24 | 24 | 24 | 24 |
| plastic fat*[1] | 0.5 | 3 | 10 | — | — | 5 |
| cholesteryl ester of branched fatty acid*[2] | 0.5 | 4 | 10 | — | 5 | — |
| titanium oxide | 2 | 2 | 2 | 2 | 2 | 2 |
| pigment (Red No. 202) | 2 | 2 | 2 | 2 | 2 | 2 |
| pigment (Red No. 204) | 1 | 1 | 1 | 1 | 1 | 1 |
| pigment (Yellow No. 4 A1 lake) | 3 | 3 | 3 | 3 | 3 | 3 |
| anti-oxidizing agent | adequate amount | adequate amount | adequate amount | adequate amount | adequate amount | adequate amount |
| perfume | adequate amount | adequate amount | adequate amount | adequate amount | adequate amount | adequate amount |

(Note)
*[1] Plastic fat obtained according to the following synthesis method. A mixed oil composed of 50 wt. % of a triglyceride of behenic acid and 50 wt. % of safflower oil was reacted in the presence of a sodium methylate catalyst in an amount of 0.1 wt. % based on the oil at 80° C. for 30 minutes to obtain an ester-exchanged oil. This ester-exchanged oil was dissolved in n-hexane in an amount of 4 ml per g of the oil, followed by cooling from 40° C. to 28° C. with stirring. The precipitated high-melting part mainly composed of a trisaturated triglyceride (yield: 14% based on the ester-exchanged oil) was filtered off. The solvent was distilled off from the filtrate according to a customary method. The residue was dissolved in acetone in an amount of 5 ml per g of the residue, followed by cooling from 30° C. to 10° C. with stirring. The precipitated desired fraction was collected. The solvent was distilled off from the fraction. Deodorizing was effected according to a customary method. Thus a plastic fat was obtained.
*[2] Cholesteryl ester of a branched fatty acid prepared from Emery 875 isostearic acid (manufactured by Emergy Industries, Inc., U.S.A.) and cholesterol.

TABLE 19

| Test item | Specimen code | | | | | |
|---|---|---|---|---|---|---|
| | Present invention | | | Comparative | | |
| | L-1 | L-2 | L-3 | L-4 | L-5 | L-6 |
| Spread | ○ | ● | ● | △ | △ | ○ |
| Bonding | ○ | ● | ● | △ | △ | ○ |
| Smoothness | ○ | ● | ● | △ | △ | ○ |
| Stickiness | ○ | ● | ● | △ | △ | ○ |
| Fit | ● | ● | ● | × | ○ | △ |
| Color fading | ○ | ● | ● | × | △ | △ |
| Blurring resistance | ● | ● | ● | × | ○ | △ |

(Note) Evaluation Standard
● : at least 8 of 10 panelists gave good evaluation.
○ : at least 6 of 10 panelists gave good evaluation.
△ : at least 4 of 10 panelists gave good evaluation.
× : at most 3 of 10 panelists gave good evaluation.

These results show that the preparations according to the present invention are excellent feeling in their use (spread, bonding, and smoothness) and wear (color fading and blurring resistance).

EXAMPLE 10

Eyebrow Pencil

Eyebrow pencils having compositions as shown in Table 20 were prepared according to the method as described below. The performance evaluation of them was conducted by 10 professional panelists.

Results are shown in Table 21.

TABLE 20

| Composition | Specimen code | | | | | |
|---|---|---|---|---|---|---|
| | Present invention | | | Comparative | | |
| | I-1 | I-2 | I-3 | I-4 | I-5 | I-6 |
| Japan wax | 11 parts | 9 | 6 | 11 | 11 | 6 |
| hardened tallow | 10.5 | 8 | 6 | 11 | 11 | 6 |
| beeswax | 5 | 5 | 5 | 5 | 5 | 5 |
| paraffin | 5 | 5 | 5 | 5 | 5 | 5 |
| stearic acid | 15 | 15 | 15 | 15 | 15 | 15 |
| lanolin | 2.5 | 1 | — | 3 | — | 3 |
| plastic fat | 0.5 | 5 | 10 | — | — | 10 |
| cholesteryl ester of branched fatty acid | 0.5 | 2 | 3 | — | 3 | — |
| black iron oxide | 30 | 30 | 30 | 30 | 30 | 30 |
| red iron oxide | 10 | 10 | 10 | 10 | 10 | 10 |
| titanium oxide | 10 | 10 | 10 | 10 | 10 | 10 |

Preparation Method

Components were heated at 80° C. and repeatedly kneaded with a roll mill. The kneaded mass was cooled to room temperature and extruded into a core from a nozzle with a compression injection machine. The core was mounted on a wooden part having a groove with a core shape, followed by bonding, combining, and cutting. Thus a pencil-shaped product was prepared.

TABLE 21

| Test item | Specimen code | | | | | |
|---|---|---|---|---|---|---|
| | Present invention | | | Comparative | | |
| | I-1 | I-2 | I-3 | I-4 | I-5 | I-6 |
| Easiness in drawing | ○ | ● | ● | △ | △ | ○ |
| Softness | ● | ● | ● | △ | △ | ○ |
| Smoothness | ● | ● | ● | × | ○ | ○ |
| Unevenness | ○ | ● | ● | × | ○ | △ |

TABLE 21-continued

| | Specimen code | | | | | |
|---|---|---|---|---|---|---|
| | Present invention | | | Comparative | | |
| Test item | I-1 | I-2 | I-3 | I-4 | I-5 | I-6 |
| Wear | ○ | ○ | ● | × | ○ | △ |

(Note) Evaluation Standard
● : at least 8 of 10 panelists gave good evaluation.
○ : at least 6 of 10 panelists gave good evaluation.
△ : at least 4 of 10 panelists gave good evaluation.
× : at most 3 of 10 panelists gave good evaluation.

These results show that the preparations according to the present invention are excellent in feeling in their use (spreadability and bonding) and wear (kink and falling off).

These results show that the preparations according to the present invention are excellent in feeling in their use (spread, bonding, and smoothness) and wear (color fading and blurring resistance).

EXAMPLE 11

Solid Powder Eye Shadow

Solid powder eye shadows having compositions as shown in Table 22 were prepared according to the method as described below. The impact resistance evaluation of them as well as the performance evaluation of them by 10 professional panelists was conducted.

Results are shwon in Table 23.

TABLE 22

| | Specimen code | | | | | |
|---|---|---|---|---|---|---|
| | Present invention | | | Comparative | | |
| Composition | P-1 | P-2 | P-3 | P-4 | P-5 | P-6 |
| talc | 15 parts | 15 | 15 | 15 | 15 | 15 |
| sericite | 30 | 30 | 30 | 30 | 30 | 30 |
| micaceous titanium | 35 | 35 | 35 | 35 | 35 | 35 |
| ultramarine | 5 | 5 | 5 | 5 | 5 | 5 |
| iron oxide | 2 | 2 | 2 | 2 | 2 | 2 |
| squalane | 8 | 8 | 4 | 8 | 8 | 8 |
| hardened palm oil | 1.5 | 1 | — | 2 | 2 | — |
| lanolin | 1.5 | 1 | — | 2 | — | 2 |
| paraffin | 1 | 1 | 1 | 1 | 1 | 1 |
| plastic fat | 0.5 | 1 | 4 | — | — | 2 |
| cholesteryl ester of branched fatty acid | 0.5 | 1 | 4 | — | 2 | — |

Preparation Method

Powdery components were stirred and mixed, and sprayed with oily components which were heated and homogeneously dissolved, followed by further stirring. Thereafter, the resulting mixture was pulverized and compression-molded with a molding machine to obtain a solid powder eye shadow.

TABLE 23

| | Specimen code | | | | | |
|---|---|---|---|---|---|---|
| | Present invention | | | Comparative | | |
| Test item | P-1 | P-2 | P-3 | P-4 | P-5 | P-6 |
| Spreadability | ○ | ● | ● | △ | △ | ○ |
| Bonding | ○ | ● | ● | △ | ○ | △ |
| Kink | ● | ● | ● | × | ○ | △ |
| Falling off | ● | ● | ● | × | ○ | △ |

(Note) Evaluation Standard
● : at least 8 of 10 panelists gave good evaluation.
○ : at least 6 of 10 panelists gave good evaluation.
△ : at least 4 of 10 panelists gave good evaluation.
× : at most 3 of 10 panelists gave good evaluation.

The embodiments of the invention in which an exclusive property or privilege is claimed are defined as follows:

1. A solid cosmetic preparation comprising a blend of (A) from 99.9 to 90 percent by weight of at least one cosmetic component and (B) from 0.1 to 10 percent by weight of a mixture of triglycerides, said mixture of triglycerides comprising mixed acid triglycerides having as fatty acid residues in the same molecule, (a) at least one straight chain, saturated $C_{20}$-$C_{26}$ fatty acid group and (b) at least one unsaturated $C_{16}$-$C_{22}$ fatty acid group, said fatty acid residues of said mixture of triglycerides comprising 15 to 70 percent by weight of straight chain, saturated $C_{20}$-$C_{26}$ fatty acid groups and 20 to 60 percent by weight of unsaturated $C_{16}$-$C_{22}$ fatty acid groups, said cosmetic component (A) being different from said mixture of triglycerides (B) and the saturated fatty acid residues of said mixed acid triglycerides not having a branched chain.

2. A solid cosmetic preparation as claimed in claim 1, which further comprises an alpha-mono(methyl-branched alkyl)glyceryl ether of the formula (1)

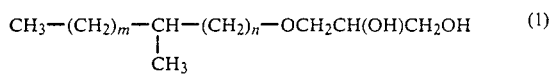

$$CH_3-(CH_2)_m-\underset{\underset{CH_3}{|}}{CH}-(CH_2)_n-OCH_2CH(OH)CH_2OH \quad (1)$$

in which m is an integer of 2 to 14, n is an integer of 3 to 11 and the total of m and n is 9 to 21.

3. A solid cosmetic preparation as claimed in claim 2, which comprises 0.1 to 10 percent by weight of said alpha-mono(methyl-branched alkyl)glyceryl ether.

4. A solid cosmetic preparation as claimed in claim 1, which further comprises a cholesteryl ester of a branched fatty acid of the formula (2)

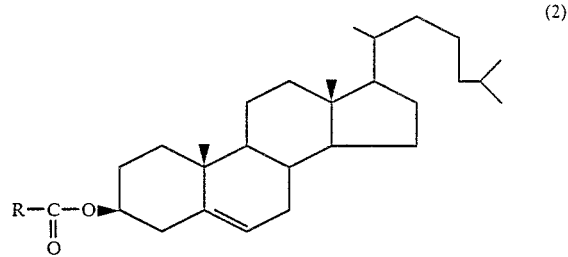

(2)

in which R is a saturated aliphatic hydrocarbon group having 11 to 23 carbon atoms and at least one alkyl substituent between the carboxyl-bonded position and the center of the main chain thereof.

5. A solid cosmetic preparation as claimed in claim 4, which comprises 0.01 to 50 percent by weight of said cholesteryl ester.

6. A solid cosmetic preparation as claimed in claim 1 wherein the fatty acid residues of said mixture of triglycerides comprise 30 to 70 percent by weight of straight chain, saturated $C_{20}$-$C_{26}$ fatty acid groups.

7. A solid cosmetic preparation as claimed in claim 1, wherein said mixed acid triglycerides have two saturated $C_{20}$-$C_{26}$ fatty acid groups and one unsaturated $C_{16}$-$C_{22}$ fatty acid group.

8. A solid cosmetic preparation as claimed in claim 1, wherein the saturated fatty acid is selected from the group consisting of arachic acid and behenic acid and said unsaturated fatty acid is selected from the group consisting of oleic acid, linolic acid and linolenic acid.

9. A solid cosmetic preparation as claimed in claim 1 in which said cosmetic component (A) comprises at least one powder which is dispersed in said mixture of triglycerides (B).

10. A solid cosmetic preparation as claimed in claim 1 in which said cosmetic component (A) comprises a pigment.

11. A solid cosmetic preparation as claimed in claim 1 in which said cosmetic component (A) comprises at least one material selected from the group consisting of cosmetic fats, cosmetic oils, cosmetic waxes, pigments and perfumes.

12. A solid cosmetic preparation as claimed in claim 1 in which the balance of said mixture of triglycerides is triglycerides having fatty acid residues having at least 8 carbon atoms.

13. A solid cosmetic preparation as claimed in claim 1, wherein said mixture of triglycerides is present in an amount of 10 percent by weight of said solid cosmetic preparation and said fatty acid residues comprise 52 percent by weight behenic acid and 32.4 percent by weight oleic acid.

14. A solid cosmetic preparation comprising a blend of (A) from 99.9 to 20 percent by weight of at least one cosmetic component and (B) from 0.1 to 80 percent by weight of a fat composition comprising a mixture of triglycerides, said mixture of triglycerides comprising at least 35 percent by weight of said fat composition and containing mixed acid triglycerides having as fatty acid residues in the same molecule,
(a) at least one straight chain, saturated $C_{20}$–$C_{26}$ fatty acid group and
(b) at least one unsaturated $C_{16}$–$C_{22}$ fatty acid group, said fatty acid residues of said mixture of triglycerides comprising 15 to 70 percent by weight of straight chain, saturated $C_{20}$–$C_{26}$ fatty acid groups and 20 to 60 percent by weight of unsaturated $C_{16}$–$C_{22}$ fatty acid groups, said cosmetic component (A) being different from said fat composition (B) and the saturated fatty acid residues of said mixed acid triglycerides not having a branched chain.

15. A solid cosmetic preparation as claimed in claim 14 in which the amount of said mixture of triglycerides is from 35 to 50 percent by weight of said fat composition.

16. A solid cosmetic preparation as claimed in claim 15 in which said mixture of triglycerides is at least 45 percent by weight of said fat composition.

17. A solid cosmetic preparation as claimed in claim 16 in which the balance of said mixture of triglycerides is triglycerides having fatty acid residues having from 16 to 24 carbon atoms.

18. A solid cosmetic preparation comprising a blend of (A) 90 percent by weight of at least one cosmetic component and (B) 10 percent by weight of a mixture of triglycerides, said mixture of triglycerides comprising mixed acid triglycerides having as fatty acid residues in the same molecule,
(a) at least one straight chain, saturated $C_{20}$–$C_{26}$ fatty acid group and
(b) at least one unsaturated $C_{16}$–$C_{22}$ fatty acid group, said fatty acid residues of said mixture of triglycercides comprising 15 to 70 percent by weight of straight chain, saturated $C_{20}$–$C_{26}$ fatty acid groups and 20 to 60 percent by weight of unsaturated $C_{16}$–$C_{22}$ fatty acid groups, said cosmetic component (A) being different from said mixture of triglycerides (B) and the saturated fatty acid residues of said mixed acid triglycerides not having a branched chain.

* * * * *